United States Patent
Ao et al.

(10) Patent No.: US 10,582,714 B2
(45) Date of Patent: *Mar. 10, 2020

(54) NUTRITIONAL COMPOSITIONS AND METHODS FOR PROMOTING COGNITIVE DEVELOPMENT

(71) Applicant: Mead Johnson Nutrition Company, Chicago, IL (US)

(72) Inventors: Zihua Ao, Newburgh, IN (US); Carol Lynn Berseth, Evansville, IN (US); Patricia Cobb, Louisville, KY (US); Juan M. Gonzalez, Newburgh, IN (US); Elisha London, Newburgh, IN (US); Minhthy Nguyen, Evansville, IN (US); James David Richards, Newburgh, IN (US); Colin Rudolph, San Francisco, CA (US); John D. Alvey, Evansville, IN (US); Yadilka Maldonado, Evansville, IN (US); Chenzhong Kuang, Lexington, MA (US); Yan Xiao, Lexington, MA (US); Dirk Hondmann, Winnetka, IL (US)

(73) Assignee: MEAD JOHNSON NUTRITION COMPANY, Evansville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/882,795

(22) Filed: Oct. 14, 2015

(65) Prior Publication Data
US 2017/0006898 A1     Jan. 12, 2017

Related U.S. Application Data

(63) Continuation-in-part of application No. 14/796,387, filed on Jul. 10, 2015.

(51) Int. Cl.
| | |
|---|---|
| *A61K 35/20* | (2006.01) |
| *A23C 17/00* | (2006.01) |
| *A61K 31/202* | (2006.01) |
| *A61K 31/715* | (2006.01) |
| *A61K 31/702* | (2006.01) |
| *A61K 38/48* | (2006.01) |
| *A61K 31/7004* | (2006.01) |
| *A61K 31/19* | (2006.01) |
| *A61K 31/714* | (2006.01) |
| *A23L 33/115* | (2016.01) |
| *A23L 33/00* | (2016.01) |
| *A23L 33/20* | (2016.01) |
| *A23L 33/17* | (2016.01) |
| *A23L 33/12* | (2016.01) |
| *A23L 33/15* | (2016.01) |
| *A23L 33/21* | (2016.01) |
| *A23L 33/19* | (2016.01) |
| *A23L 33/10* | (2016.01) |

(52) U.S. Cl.
CPC .............. *A23C 17/00* (2013.01); *A23L 33/10* (2016.08); *A23L 33/115* (2016.08); *A23L 33/12* (2016.08); *A23L 33/15* (2016.08); *A23L 33/17* (2016.08); *A23L 33/19* (2016.08); *A23L 33/20* (2016.08); *A23L 33/21* (2016.08); *A23L 33/40* (2016.08); *A61K 31/19* (2013.01); *A61K 31/202* (2013.01); *A61K 31/702* (2013.01); *A61K 31/7004* (2013.01); *A61K 31/714* (2013.01); *A61K 31/715* (2013.01); *A61K 35/20* (2013.01); *A61K 38/482* (2013.01); *A23V 2002/00* (2013.01); *C12Y 304/21* (2013.01)

(58) Field of Classification Search
CPC ........ A23V 2002/00; A23V 2200/3202; A23V 2200/32; A23V 2250/1868; A23L 33/135; A23L 33/40; A23L 33/10; A23L 33/19; A23L 33/18; A23L 33/115; A23L 33/20; A23L 33/17; A23L 33/12; A23L 33/15; A23L 33/21; A23C 21/06; A61K 35/20; A61K 31/19; A61K 31/714
See application file for complete search history.

(56) References Cited

U.S. PATENT DOCUMENTS

| | | |
|---|---|---|
| 4,791,193 A | 12/1988 | Okonogi et al. |
| 5,374,567 A | 12/1994 | Cartagena |
| 5,397,591 A | 3/1995 | Kyle |
| 5,550,156 A | 8/1996 | Kyle |
| 5,591,479 A | 1/1997 | Ponroy |

(Continued)

FOREIGN PATENT DOCUMENTS

| | | |
|---|---|---|
| CN | 101316521 A | 12/2008 |
| CN | 101370395 A | 2/2009 |

(Continued)

OTHER PUBLICATIONS http://www.healthofchildren.com/C/Cognitive-Development.html, retrieved online Feb. 22, 2018.*

(Continued)

*Primary Examiner* — Hong T Yoo
(74) *Attorney, Agent, or Firm* — Troutman Sanders LLP; Ryan Schneider; Chris Davis

(57) ABSTRACT

A method for enhancing cognitive development in a pediatric subject involving administering to the subject a nutritional composition which includes up to 7 g/100 Kcal of a fat or lipid; up to 5 g/100 Kcal of a protein or protein equivalent source; 0.25 g/100 Kcal to 16 g/100 Kcal of buttermilk; 5 mg/100 Kcal to 90 mg/100 Kcal of a source of long chain polyunsaturated fatty acid; and 0.015 g/100 Kcal to 1.5 g/100 Kcal of a prebiotic.

12 Claims, No Drawings

(56) References Cited

U.S. PATENT DOCUMENTS

| | | | |
|---|---|---|---|
| 5,686,491 | A | 11/1997 | Sherwood |
| 5,709,888 | A | 1/1998 | Gil et al. |
| 5,849,885 | A | 12/1998 | Nuyens |
| 5,861,491 | A | 1/1999 | Nuijens |
| 5,919,913 | A | 7/1999 | Nuyens |
| 6,500,472 | B2 | 12/2002 | Uchida et al. |
| 6,620,326 | B1 | 9/2003 | Lihme |
| 6,977,046 | B2 | 12/2005 | Hubbuch |
| 7,354,896 | B2 | 4/2008 | Kirwin et al. |
| 7,368,141 | B2 | 5/2008 | Lihme |
| 7,812,138 | B2 | 10/2010 | Lihme |
| 7,851,450 | B2 | 12/2010 | Beerman et al. |
| 7,897,541 | B2 | 3/2011 | Iwasaki et al. |
| 7,951,410 | B2 | 5/2011 | McMahon et al. |
| 8,445,053 | B2 | 5/2013 | Holst et al. |
| 2008/0003329 | A1 | 1/2008 | Rueda et al. |
| 2008/0003330 | A1 | 1/2008 | Rueda et al. |
| 2008/0125346 | A1* | 5/2008 | Beermann ............ A61K 31/201 424/439 |
| 2011/0009349 | A1 | 1/2011 | Fonterra |
| 2011/0293783 | A1 | 12/2011 | Wittke |
| 2011/0293784 | A1 | 12/2011 | Wittke |
| 2012/0171178 | A1* | 7/2012 | Fleith .................... A23L 33/135 424/93.45 |
| 2012/0171328 | A1* | 7/2012 | Banavara ............... A23C 11/04 426/61 |
| 2012/0269929 | A1 | 10/2012 | Lippman et al. |
| 2012/0276057 | A1 | 11/2012 | Nestle |
| 2013/0071446 | A1 | 3/2013 | Van Der Beek et al. |
| 2013/0150306 | A1 | 6/2013 | Wittke |
| 2014/0199265 | A1 | 7/2014 | Kuang et al. |
| 2015/0037455 | A1 | 2/2015 | Chichlowski et al. |

FOREIGN PATENT DOCUMENTS

| | | |
|---|---|---|
| CN | 102215702 A | 10/2011 |
| EP | 0183572 | 7/1992 |
| EP | 0484266 | 7/1992 |
| EP | 0433113 | 5/1995 |
| EP | 2046149 | 11/2010 |
| EP | 2251030 | 11/2010 |
| EP | 2251031 | 11/2010 |
| EP | 2258216 | 12/2010 |
| EP | 2258217 | 12/2010 |
| EP | 2258218 | 12/2010 |
| EP | 2594282 | 5/2013 |
| EP | 2638810 | 9/2013 |
| JP | H09172962 A | 7/1997 |
| WO | 1992000799 | 1/1992 |
| WO | 1992000799 | 5/1997 |
| WO | 2002018237 | 3/2002 |
| WO | 2005051091 | 6/2005 |
| WO | 2007073178 | 6/2007 |
| WO | 2010139701 | 12/2010 |
| WO | 2011069987 | 6/2011 |
| WO | 2011115476 | 9/2011 |
| WO | 2011150337 | 12/2011 |

OTHER PUBLICATIONS

Armand, M., et al., "Effect of Human Milk or Formula on Gastric Function and Fat Digestion in the Premature Infant," Pediatric Research (1996) 40, 429-437.

Huang, M., et al., "Comparison of Lipid in Milk and Breast Milk," China Dairy Industry, vol. 19, No. 4, Aug. 29, 1991.

Michalski, M.C., et al., "Size Distribution of Fat Globules in Human Colostrum, Breast Milk, and Infant Formula," Journal of Dairy Science, vol. 88, No. 6, Dec. 31, 2005.

Fuller, K.L., et al., "Milk fat globule membrane isolated from buttermilk or whey cream and their lipid components inhibit infectivity of rotavirus in vitro," J. Dairy Sci. 96:1-10, 2013.

Gassi, J., et al., 'Heat treatment of cream affects the physicochemical properties of sweet buttermilk, Dairy Sci. Technol. 88 (2008) 369-385.

Morin, P., et al., "A comparative study of the fractionation of regular buttermilk and whey buttermilk by microfiltration," Journal of Food Engineering, vol. 77, Issue 3, Dec. 2006, 521-528.

Morin, P., et al. "Effect of processing on the composition and microstructure of buttermilk and its milk fat globule membranes." International Dairy Journal 17.10 (2007): 1179-1187.

Morin, P., et al., "Microfiltration of Buttermilk and Washed Cream Buttermilk for Concentration of Milk Fat Globule Membrane Components," J. Dairy Sci. 90:2132-2140, 2007.

Sodini, I., et al., "Compositional and Functional Properties of Buttermilk: A Comparison Between Sweet, Sour, and Whey Buttermilk1," J. Dairy Sci. 89:525-536, 2006.

Takamizawa, K., et al., "Gangliosides of Bovine Buttermilk—Isolation and Characterization of a novel monosialoganglioside with a new branching structure," The Journal of Biological Chemistry, vol. 261, No. 12, Issue of Apr. 25, pp. 5625-5630, 1986.

Vanderghem, C., et al., "Milk fat globule membrane and buttermilks: from composition to valorization," Biotechnol. Agron. Soc. Environ. 2010 14(3), 485-500.

Awad, K., et al., "Effects of exercise and nutritional intake on sleep architecture in adolescents," Sleep Breath. Mar. 2013; 17(1): 117-124.

Bemiller, J.N., "An Introduction to Pectins: Structure and Properties, Chemistry and Function of Pectins" Chapter 1; 1986.

Brenna, J., et al., "Docosahexaenoic and arachidonic acid concentrations in human breast milk worldwide1-4," Am J. Clin Nutr 2007;85:1457-1464.

Droro, D., et al., "Effect of vitamin B12 deficiency on neurodevelopment in infants: current knowledge and possible mechanisms," Nutr Rev. 2008, 66: 250-255.

Fanaro et al., "Acidic Oligosaccharides from Pectin Hydrolysate as New Component for Infant Formulae: Effect on Intestinal Flora, Stool Characteristics, and pH", Journal of Pediatric Gastroenterology and Nutrition, 41: 186-190, Aug. 2005.

Fenzl, T., et al., "Sleep disturbances in highly stress reactive mice: Modeling endophenotypes of major depression," BMC Neuroscience 2011, 12:29.

Garcia, C., et al., "Phospholipid fingerprints of milk from different mammalians determined by 31P NMR: towards specific interest in human health," Food Chem. 2012, 135: 1777-1778.

Gurnida, D., et al., "Association of complex lipids containing gangliosides with cognitive development of 6-month-old infants," Early Hum Dev. 2012, 88: 595-601.

Herlenius, E., et al., "Development of neurotransmitter systems during critical periods," Experimental Neurology 190 (2004) S8-S21.

IBFAN "Breast-Feeding and Brain Development (Cognitive Development)", Information Sheet-9, IBFAN Asia Pacific/Breastfeeding Promotion Network of India (BPNI), Feb. 2005, p. 1-2.

Kamemori, N., et al., "Trans-Endothelial and Trans-Epithelial Transfer of Lactoferrin in the Brain through BBB and BCSFB in Adult Rats," J. Vet. Med. Sci. 70(3): 313-315, 2008.

Kuhara, T., et al., "Oral Administration of Lactoferrin Increases NK Cell Activity in Mice via Increased Production of IL-18 and Type I IFN in the Small Intestine," Journal of Interferon & Cytokine Research 26:489-499 (2006).

Kunz, et al., Oligosaccharides in Human Milk: Structure, Functional, and Metabolic Aspects, Ann. Rev. Nutr. 20: 699-722 (2000).

Ling J. et al. "Perspectives on Interactions Between Lactoferrin and Bacteria," Biochemistry and Cell Biology, pp. 275-281 (2006).

Lonnerdal, B., "Nutritional roles of lactoferrin," Curr Opin Clin Nutr Metal Care. 2009, 12: 1363-1950.

Lopez C., et al., "Human milk fat globules: Polar lipid composition and in situ structural investigations revealing the heterogeneous distribution of proteins and the lateral segregation of sphingomyelin in the biological membrane," Colloids and Surfaces B: Biointerfaces 83 (2011) 29-41.

Martinez, M., "Tissue levels of polyunsaturated fatty acids during early human development," J. Pediatr 1992;120: S129-38.

Martinez, M., et al., "Fatty Acid Composition of Human Brain Phospholipids During Normal Development," J. Neurochem. 71, 2528-2533 (1998).

(56) References Cited

OTHER PUBLICATIONS

Mather, I., "A Review and Proposed Nomenclature for Major Proteins of the Milk-Fat Globule Membrane1,2," 2000 J Dairy Sci 83: 203-247.

McJarrow, P., et al., "Influence of dietary gangliosides on neonatal brain development," Nutrition Reviews vol. 67 (8):451-463.

Menard, O., et al., "Buffalo vs. cow milk fat globules: Size distribution, zeta-potential, compositions in total fatty acids and in polar lipids from the milk fat globule membrane," Food Chemistry 120 (2010) 544-551.

Mintel, "Golden Growing-Up Formula Goat Milk Powder," Database Accession No. 1694223, Jan. 2012 XP002730875.

Mintel, "Growing-Up Milk Powder (Stage 3) with Lactoferyin," Database Accession No. 2081489, Jan. 2012 XP002730876.

Mintel, "Growing-Up Milk for Children," Database Accession No. 2085763, Jun. 2013 XP002730877.

Mintel, "New Birth Formula," Database Accession No. 1249000, Jan. 2010 XP002673470.

Mintel, "Stage 2 Infant Formula," Database Accession No. 2032623, Mar. 2013 XP002730874.

Monaco, M., et al., "Addition of Polydextrose and Galactooligosaccharide to Formula Does Not Affect Bacterial Translocation in the Neonatal Piglet," JPGN 2011;52: 2010-216.

Morgan, B., et al., "Effects of Administration of N-Acetylneuraminic Acid (NANA) on Brain NANA Content and Behavior," J. Nutr. 110: 416-424, 1980.

Morgan, B. L., et al., "Effects of environmental stimulation on brain N-acetylneuraminic acid content and behavior." J Nutr 110(3): 425-432, 1980.

Mulder, A., et al., "Bovine lactoferrin supplementation supports immune and antioxidant status in healthy human males," Nutrition Research 28 (2008) 583-589.

Ochoa, T., et al., "Impact of Lactoferrin Supplementation on Growth and Prevalence of Giardia Colonization in Children," Brief Report CID 2008:46 (Jun. 15).

Precht, D., et al., "C18:1, C18:2 and C18:3 trans and cis fatty acid isomers including conjugated cis 9, trans 11 linoleic acid (CLA) as well as total fat composition of German human milk lipids," Nahrung, 43 (4): 233-244. 1999.

Rahman, M.D., M. et al., "Growth promotion and cell binding ability of bovine lactoferrin to Bifidobacterium longum," Anaerobe, 15(4): 133-137.

Rai, D., et al., "Longitudinal Changes in Lactoferrin Concentrations in Human Milk: A Global Systematic Review," Crit Rev Food Sci & Nutr, 54:12, 1539-1547.

Ribeiro, T., et al., "Stool Pattern Changes in Toddlers Consuming a Follow-on Formula Supplemented With Polydextrose and Galactooligosaccharides," JPGN 2012;54: 288-290.

Salvini, F., et al., "A Specific Prebiotic Mixture Added to Starting Infant Formula Has Long-Lasting Bifidogenic Effects1-3," J. Nutr. 141: 1335-1339, 2011.

Savino, F., et al., "Lactobacillus reuteri DSM 17 938 in Infantile Colic: A Randomized, Double-Blind, Placebo-Controlled Trial," Pediatrics published online Aug. 16, 2010; DOI 10.1542/peds.2010-0433.

Scalabrin, D., et al., "New Prebiotic Blend of Polydextrose and Galacto-oligosaccharides Has a Bifidogenic Effect in Young Infants," JPGN 2012;54: 343-352.

Svennerholm, L., et al., "Chromatographic Separation of Human Brain Gangliosides," Journal of Neurochemistry, 1963, vol. 10, pp. 613-623.

Thomas, C., et al., "Histamine Derived from Probiotic Lactobacillus reuteri Suppresses TNF via Modulation of PKA and ERK Signaling," PLoS One 7(2):2012.

Timby, N., et al., "Neurodevelopment, nutrition, and growth until 12 mo of age in infants fed a low-energy, low-protein formula supplemented with bovine milk fat globule membranes: a randomized controlled trial1-3," Am J Clin Nutr 2014;99:860-868.

Veereman-Wauters, G., et al., "Milk fat globule membrane (INPULSE) enriched formula milk decreases febrile episodes and may improve behavioral regulation in young children," Nutrition 28 (2012) 749-752.

Veereman-Wauters, G., et al., "Physiological and Bifidogenic Effects of Prebiotic Supplements in Infant Formulai," JPGN 2011;52: 763-771.

Yadomae, T., "Structure and biological activities of fungal beta-1,3-glucans." Yakugaku Zasshi. 2000;120:413431.

Zavaleta, N., et al., "Efficacy of an MFGM-enriched Complementary Food in Diarrhea, Anemia, and Micronutrient Status in Infants," JPGN 2011;53: 561-568.

Ziegler, E., et al., "Term Infants Fed Formula Supplemented With Selected Blends of Prebiotics Grow Normally and Have Soft Stools Similar to Those Reported for Breast-fed Infants," Journal of Pediatric Gastroenterology and Nutrition 44:359-364 (2007).

Fee et al. "Capture of lactoferrin and lactoperoxidase from raw whole milk by cation exchange chromatography" Separation and Purification Technology 48 (2006) 143-149.

Wang, Y., et al., "Milk Biochemistry," Dec. 31, 1995, pp. 41, 51-72.

\* cited by examiner

NUTRITIONAL COMPOSITIONS AND METHODS FOR PROMOTING COGNITIVE DEVELOPMENT

TECHNICAL FIELD

The present disclosure relates to a method for promoting cognitive development in children by providing them with nutritional compositions that include certain combinations of functional ingredients at levels designed to promote and support immune function, gastrointestinal health and brain function, all of which can combine to improve cognitive development. More particularly, the disclosed nutritional compositions include buttermilk, long chain polyunsaturated fatty acids, and prebiotics, optionally also in combination with one or more of lactoferrin, short chain fatty acids and vitamin B12. The nutritional compositions described herein are suitable for administration to pediatric subjects to support and promote cognitive development.

BACKGROUND

Human milk contains a number of components that contribute to the growth and development of the brain in infants. But, cow's milk and many commercially available infant formulas that are based on cow's milk provide lower than desirable amounts of some of these components, like long chain polyunsaturated fatty acids, lactoferrin and polar lipids. Therefore, there is a need to provide a formula matrix that more closely mimics the composition and qualities of human milk in order to optimize brain growth and development in infants and children.

Thus, it would be useful to provide methods and nutritional compositions that are able to provide improved neurological health and function, including cognition, language development and motor skills in early life. It would also be useful to promote and support immune function, gastrointestinal health and brain function as a way of achieving these results.

Accordingly, the present disclosure provides a method for supporting cognitive development in a subject, involving administering to the subject a nutritional composition which includes buttermilk, long chain polyunsaturated fatty acids, and prebiotics, optionally also in combination with one or more of lactoferrin, short chain fatty acids and vitamin B12. In some embodiments, the nutritional composition also includes a fat or lipid, carbohydrate and protein or protein equivalent source.

BRIEF SUMMARY

Briefly, the present disclosure is directed to compositions and methods for supporting and promoting functional neuronal maturation in pediatric subjects. The methods involve administering compositions that comprise the combination of buttermilk, long chain polyunsaturated fatty acids (LCPUFAs), such as docosahexaenoic acid (DHA), and a prebiotic composition. More particularly, in certain embodiments, the nutritional composition of the present disclosure comprises:

up to about 7 g/100 Kcal of a fat or lipid;
up to about 5 g/100 Kcal of a protein or protein equivalent source;
about 0.25 g/100 Kcal to about 16 g/100 Kcal of buttermilk;
about 5 mg/100 Kcal to about 90 mg/100 Kcal of LCPUFA; and
about 0.015 g/100 Kcal to about 1.5 g/100 Kcal of a prebiotic.

In some embodiments, the nutritional composition further comprises about 5 mg/100 Kcal to about 300 mg/100 Kcal of lactoferrin. The pediatric subject may be an infant or a child, and the nutritional composition may be provided as an infant formula or growing up milk (which is meant to include follow-on formula or follow-up formula).

Buttermilk, in the context of the present disclosure, refers to an aqueous by-product of different milk fat manufacturing processes, especially the butter making process, and includes dry buttermilk, which is defined as having a protein content of not less than 30%, and dry buttermilk product, having a protein content of less than 30%. Both types of dry buttermilk have a minimum fat content of 4.5% and a moisture maximum of 5%. Cultured buttermilk is also within the contemplation of this disclosure, in some embodiments. Buttermilk contains components such as lactose, minerals, oligosaccharides, immunoglobulins, milk lipids, and milk proteins, each of which is found in the aqueous phase during certain dairy cream processing steps. It is also a concentrated source of milk fat globule membrane (MFGM) components compared to other milk sources. Buttermilk can be obtained through different processes, such as:

Churning of cream during production of butter or cheese. The cream can be whey cream and/or regular cream during butter production (ilt is understood that the cream referenced herein will have originated from raw or whole milk, therefore the processing steps to first produce cream from these materials is omitted). Many different processing and/or purification steps can be applied to the resulting aqueous phase (i.e. standardizing protein concentrations, enrichment of lipid and/or phospholipid concentrations). As these modifications do not change the fundamental identity of the material, all materials resulting from these modifications are within the contemplation of this disclosure.

Production of variants of butter such as sweet cream butter, clarified butter, butterfat.

Production of anhydrous milk fat (butter oil) from cream or butter. The removal of the fat-free dry matter and water from milk, cream, or butter, which is required to make anhydrous milk fat, yields buttermilk as a byproduct. The removal can be accomplished by mechanical (i.e. cream concentrator, oil concentrator) and/or chemical (i.e. pH manipulation) induced separation.

Production of anhydrous milk fat (butter oil) from blending the secondary skim and β-serum (and/or butter serum) streams together that comes from separation of cream and oil concentration, respectively.

The milk fat globule membrane is comprised of a trilayer lipid structure that includes a complex mixture of phospholipids, proteins, glycoproteins, triglycerides, polar lipids, cholesterol, enzymes and other components which are generally not abundant in conventional infant formulas and growing-up milks. In addition to the polar lipids, the outer layer of MFGM contains other milk fat associated proteins, such as mucin 1 (MUC-1), mucin (MUC-15), butyrophilin, cluster of differentiation 36 (CD36), xanthine dehydrogenase/oxidase (XDH/XO), periodic acid Schiff 6/7, immunoglobulin M, adipophilin and FA-binding protein. These proteins only constitute a small amount of total milk protein, but they may play different and important functional roles.

The polar lipids found in MFGM are composed of:
(i) Glycerophospholipids such as phosphatidylcholine (PC), phosphatidylethanolamine (PE), phosphatidylserine (PS), and phosphatidylinositol (PI), and their derivatives and
(ii) Sphingoids or sphingolipids such as sphingomyelin (SM) and glycosphingolipids comprising cerebrosides (neutral glycosphingolipids containing uncharged sugars) and the gangliosides (GG, acidic glycosphingolipids containing sialic acid) and their derivatives.

Phosphatidylethanolamine is a phospholipid found in biological membranes, particularly in nervous tissue such as the white matter of brain, nerves, neural tissue, and in spinal cord, where it makes up 45% of all phospholipids. Sphingomyelin is a type of sphingolipid found in animal cell membranes, especially in the membranous myelin sheath that surrounds some nerve cell axons. It usually consists of phosphocholine and ceramide, or a phosphoethanolamine head group; therefore, sphingomyelins can also be classified as sphingophospholipids. In humans, SM represents ~85% of all sphingolipids, and typically makes up 10-20 mol % of plasma membrane lipids. Sphingomyelins are present in the plasma membranes of animal cells and are especially prominent in myelin, a membranous sheath that surrounds and insulates the axons of some neurons.

LCPUFAs such as DHA are omega-3 fatty acids that are a primary structural component of the human brain, cerebral cortex, skin, sperm, testicles and retina. DHA can be synthesized from alpha-linolenic acid or obtained directly from maternal milk or fish oil. DHA is the most abundant omega-3 fatty acid in the brain and retina. DHA comprises 40% of the polyunsaturated fatty acids (PUFAs) in the brain and 60% of the PUFAs in the retina. Fifty percent of the weight of a neuron's plasma membrane is composed of DHA. DHA is richly supplied during breastfeeding, and DHA levels can be high in human milk. DHA concentrations in human milk range from 0.07% to greater than 1.0% of total fatty acids, with a mean of about 0.32%. DHA levels in human milk are higher if a mother's diet is high in fish.

Prebiotics are believed to alter the production of biogenic amines and neurotransmitters within the central nervous system through their impact on the GI microbiota, and such changes may explain the beneficial effects of prebiotics on social skills, anxiety and memory functions. It is therefore believed that prebiotics may act cooperatively with the buttermilk and LCPUFAs to enhance brain development and promote neuronal maturation. In summary, the disclosed nutritional composition may play an important role during infancy and childhood by modifying intestinal microflora, optimizing brain composition, and improving a variety of brain-related behaviors and functions.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

DETAILED DESCRIPTION

Reference now will be made in detail to the embodiments of the present disclosure, one or more examples of which are set forth hereinbelow. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

The present disclosure relates generally to administration of nutritional compositions to a pediatric subject, i.e. an infant or child. Additionally, the disclosure relates to methods for improving neurological and cognitive health and development in infants and children via administration of the nutritional composition(s) disclosed herein.

"Nutritional composition" means a substance or formulation that satisfies at least a portion of a subject's nutrient requirements. The terms "nutritional(s)", "nutritional formula(s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or nutritional compositions for adults.

The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

"Pediatric subject" means a human no greater than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or full term) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, extremely low birth weight infants and preterm infants. "Preterm" means an infant born before the end of the $37^{th}$ week of gestation. "Late preterm" means an infant from between the $34^{th}$ week and the $36^{th}$ week of gestation. "Full term" means an infant born after the end of the $37^{th}$ week of gestation. "Low birth weight infant" means an infant born weighing less than 2500 grams (approximately 5 lbs, 8 ounces). "Very low birth weight infant"

means an infant born weighing less than 1500 grams (approximately 3 lbs, 4 ounces). "Extremely low birth weight infant" means an infant born weighing less than 1000 grams (approximately 2 lbs, 3 ounces).

"Child" means a subject ranging in age from 12 months to 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product, as are follow-on formulas and follow-up formulas.

The term "degree of hydrolysis" refers to the extent to which peptide bonds are broken by a hydrolysis method. The degree of protein hydrolysis for purposes of characterizing the hydrolyzed protein component of the nutritional composition is easily determined by one of ordinary skill in the formulation arts by quantifying the amino nitrogen to total nitrogen ratio (AN/TN) of the protein component of the selected formulation. The amino nitrogen component is quantified by USP titration methods for determining amino nitrogen content, while the total nitrogen component is determined by the Kjeldahl method, all of which are well known methods to one of ordinary skill in the analytical chemistry art.

The term "partially hydrolyzed" means having a degree of hydrolysis which is greater than 0% but less than about 50%.

The term "extensively hydrolyzed" means having a degree of hydrolysis which is greater than or equal to about 50%.

The term "protein-free" means containing no measurable amount of protein, as measured by standard protein detection methods such as sodium dodecyl (lauryl) sulfate-polyacrylamide gel electrophoresis (SDS-PAGE) or size exclusion chromatography. In some embodiments, the nutritional composition is substantially free of protein, wherein "substantially free" is defined hereinbelow.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age. As used herein, the term "growing-up milk" is intended to refer also to "follow-on formulas" and "follow-up formulas".

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Milk" means a component that has been drawn or extracted from the mammary gland of a mammal. In some embodiments, the nutritional composition comprises components of milk that are derived from domesticated ungulates, ruminants or other mammals or any combination thereof.

"Fat globule" refers to a small mass of fat surrounded by phospholipids and other membrane and/or serum lipids and proteins, where the fat itself can be a combination of any vegetable or animal fat.

"Polar lipids" are the main constituents of natural membranes, occurring in all living organisms. The polar lipids in milk (i.e., milk polar lipids) are mainly situated in the milk fat globule membrane. Polar lipids can be separated in the cream during milk processing, and some are further concentrated in the buttermilk fraction after, e.g., butter churning. Polar lipids are also present in sources other than milk such as eggs, meat and plants.

Polar lipids are generally divided into phospholipids and sphingolipids (including gangliosides), which are amphiphilic molecules with a hydrophobic tail and a hydrophilic head group. The glycerophospholipids consist of a glycerol backbone on which two fatty acids are esterified on positions sn-1 and sn-2. These fatty acids are more unsaturated than the triglyceride fraction of milk. On the third hydroxyl, a phosphate residue with different organic groups (choline, serine, ethanolamine, etc.) may be linked. Generally, the fatty acid chain on the sn-1 position is more saturated compared with that at the sn-2 position. Lysophospholipids contain only one acyl group, predominantly situated at the sn-1 position. The head group remains similar. The characteristic structural unit of sphingolipids is the sphingoid base, a long-chain (12-22 carbon atoms) aliphatic amine containing two or three hydroxyl groups. Sphingosine (d18:1), is the most prevalent sphingoid base in mammalian sphingolipids, containing 18 carbon atoms, two hydroxyl groups and one double bond. A ceramide is formed when the amino group of this sphingoid base is linked with, usually, a saturated fatty acid. On this ceramide unit, an organophosphate group can be bound to form a sphingophospholipid (e.g., phosphocholine in the case of sphingomyelin) or a saccharide to form the sphingoglycolipids (glycosylceramides). Monoglycosylceramides, like glucosylceramide or galactosylceramide are often denoted as cerebrosides while tri- and tetraglycosylceramides with a terminal galactosamine residue are denoted as globosides. Finally, gangliosides are highly complex oligoglycosylceramides, containing one or more sialic acid groups in addition to glucose, galactose and galactosamine.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Probiotic" means a microorganism with low or no pathogenicity that exerts a beneficial effect on the health of the host.

The term "inactivated probiotic" means a probiotic wherein the metabolic activity or reproductive ability of the referenced probiotic has been reduced or destroyed. The "inactivated probiotic" does, however, still retain, at the cellular level, its cell structure or other structure associated with the cell, for example exopolysaccharide and at least a portion its biological glycol-protein and DNA/RNA structure. As used herein, the term "inactivated" is synonymous with "non-viable".

"Prebiotic" means a non-digestible food ingredient that beneficially affects the host by selectively stimulating the growth and/or activity of one or a limited number of bacteria in the digestive tract that can improve the health of the host.

A component is said to be "inherent", "endogenous", or present from "endogenous sources" if it is present in the composition in other components or ingredients of the composition, i.e., naturally present in such other components. Contrariwise, "exogenous" refers to a component which is intentionally included in the nutritional composition of the present disclosure itself, rather than as an element of another component. For instance, "inherent inositol", "endogenous inositol" or "inositol from endogenous sources" each refer to inositol present in the composition that is not added as such, but is present in other components or ingredients of the composition; the inositol is naturally present in such other components. "Exogenous" inositol is inositol which is intentionally included in the nutritional composition of the present disclosure itself, rather than as an element of another component.

"Branched Chain Fatty Acid" ("BCFA") means a fatty acid containing a carbon constituent branched off the carbon chain. Typically the branch is an alkyl branch, especially a methyl group, but ethyl and propyl branches are also known. The addition of the methyl branch lowers the melting point compared with the equivalent straight chain fatty acid. This includes branched chain fatty acids with an even number of carbon atoms in the carbon chain. Examples of these can be isomers of tetradecanoic acid, hexadecanoic acid.

"Odd- and Branched-Chain Fatty Acid" ("OBCFA") is a subset of BCFA that has an odd number of carbon atoms and have one or more alkyl branches on the carbon chain. The main odd- and branched-chain fatty acids found in bovine milk include, but are not limited to, the isomers of tetradecanoic acid, pentadecanoic acid, hexadecanoic acid, and heptadecanoic acid. For the purposes of this disclosure, the term "BCFA" includes both branched-chain fatty acids and odd-and-branched chain fatty acids.

"Phospholipids" means an organic molecule that contains a diglyceride, a phosphate group and a simple organic molecule. Examples of phospholipids include but are not limited to, phosphatidic acid, phosphatidylethanolamine, phosphatidylcholine, phosphatidylserine, phosphatidylinositol, phosphatidylinositol phosphate, phosphatidylinositol biphosphate and phosphatidylinositol triphosphate, ceramide phosphorylcholine, ceramide phosphorylethanolamine and ceramide phosphorylglycerol. This definition further includes sphingolipids such as sphingomyelin. Glycosphingolipds are quantitatively minor constituents of the MFGM, and consist of cerebrosides (neutral glycosphingolipids containing uncharged sugars) and gangliosides. Gangliosides are acidic glycosphingolipids that contain sialic acid (N-acetylneuraminic acid (NANA)) as part of their carbohydrate moiety. There are various types of gangliosides originating from different synthetic pathways, including GM3, GM2, GM1a, GD1a, GD3, GD2, GD1b, GT1b and GQ1b (Fujiwara et al., 2012). The principal gangliosides in milk are GM3 and GD3 (Pan & Izumi, 1999). The different types of gangliosides vary in the nature and length of their carbohydrate side chains, and the number of sialic acid attached to the molecule.

"Phytonutrient" means a chemical compound that occurs naturally in plants. Phytonutrients may be included in any plant-derived substance or extract. The term "phytonutrient(s)" encompasses several broad categories of compounds produced by plants, such as, for example, polyphenolic compounds, anthocyanins, proanthocyanidins, and flavan-3-ols (i.e. catechins, epicatechins), and may be derived from, for example, fruit, seed or tea extracts. Further, the term phytonutrient includes all carotenoids, phytosterols, thiols, and other plant-derived compounds. Moreover, as a skilled artisan will understand, plant extracts may include phytonutrients, such as polyphenols, in addition to protein, fiber or other plant-derived components. Thus, for example, apple or grape seed extract(s) may include beneficial phytonutrient components, such as polyphenols, in addition to other plant-derived substances.

"β-glucan" means all β-glucan, including specific types of β-glucan, such as β-1,3-glucan or β-1,3;1,6-glucan. Moreover, β-1,3;1,6-glucan is a type of β-1,3-glucan. Therefore, the term "β-1,3-glucan" includes β-1,3;1,6-glucan.

"Pectin" means any naturally-occurring oligosaccharide or polysaccharide that comprises galacturonic acid that may be found in the cell wall of a plant. Different varieties and grades of pectin having varied physical and chemical properties are known in the art. Indeed, the structure of pectin can vary significantly between plants, between tissues, and even within a single cell wall. Generally, pectin is made up of negatively charged acidic sugars (galacturonic acid), and some of the acidic groups are in the form of a methyl ester group. The degree of esterification of pectin is a measure of the percentage of the carboxyl groups attached to the galactopyranosyluronic acid units that are esterified with methanol.

Pectin having a degree of esterification of less than 50% (i.e., less than 50% of the carboxyl groups are methylated to form methyl ester groups) are classified as low-ester, low methoxyl, or low methylated ("LM") pectins, while those having a degree of esterification of 50% or greater (i.e., more than 50% of the carboxyl groups are methylated) are classified as high-ester, high methoxyl or high methylated ("HM") pectins. Very low ("VL") pectins, a subset of low methylated pectins, have a degree of esterification that is less than approximately 15%.

As used herein, "lactoferrin from a non-human source" means lactoferrin which is produced by or obtained from a source other than human milk. For example, lactoferrin for use in the present disclosure includes human lactoferrin produced by a genetically modified organism as well as non-human lactoferrin. The term "organism", as used herein, refers to any contiguous living system, such as animal, plant, fungus or micro-organism.

As used herein, "non-human lactoferrin" means lactoferrin that has an amino acid sequence that is different than the amino acid sequence of human lactoferrin.

"Pathogen" means an organism that causes a disease state or pathological syndrome. Examples of pathogens may include bacteria, viruses, parasites, fungi, microbes or combination(s) thereof.

"Modulate" or "modulating" means exerting a modifying, controlling and/or regulating influence. In some embodiments, the term "modulating" means exhibiting an increasing or stimulatory effect on the level/amount of a particular component activity or effect. In other embodiments, "modulating" means exhibiting a decreasing or inhibitory effect on the level/amount of a particular component activity or effect.

All percentages, parts and ratios as used herein are by weight of the total formulation, unless otherwise specified.

All amounts specified as administered "per day" may be delivered in one unit dose, in a single serving or in two or more doses or servings administered over the course of a 24 hour period.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The present disclosure is directed to a method for enhancing cognitive development in a pediatric subject by administering to the pediatric subject (commonly by feeding) the nutritional compositions disclosed herein. The nutritional compositions of the present disclosure thus support and improve neurological health and development.

The nutritional composition of the present disclosure includes buttermilk.

In some embodiments, the buttermilk is included in the nutritional composition of the present disclosure at a level of about 2 grams per liter (g/L) to about 130 g/L; in other embodiments, the buttermilk is present at a level of about 5 g/L to about 100 g/L. In still other embodiments, buttermilk is present in the nutritional composition at a level of about 10 g/L to about 80 g/L. Alternatively, in certain embodiments, the buttermilk is included in the nutritional composition of the present disclosure at a level of about 0.25 grams per 100 Kcal (g/100 Kcal) to about 16 g/100 Kcal; in other embodiments, the buttermilk is present at a level of about 0.6 g/100 Kcal to about 15 g/100 Kcal. In still other embodiments, the buttermilk is present in the nutritional composition at a level of about 1.2 g/100 Kcal to about 12 g/100 Kcal.

Total phospholipids in the nutritional composition disclosed herein (i.e., including phospholipids from the buttermilk as well as other components, but not including phospholipids from plant sources such as soy lecithin, if used) is in a range of about 50 mg/L to about 2000 mg/L; in some embodiments it is about 100 mg/L to about 1000 mg/L, or about 150 mg/L to about 550 mg/L. In certain embodiments, the MFGM component also contributes sphingomyelin in a range of about 10 mg/L to about 400 mg/L; in other embodiments, it is about 30 mg/L to about 300 mg/L, or about 50 mg/L to about 200 mg/L. And, the buttermilk can also contribute gangliosides, which in some embodiments, are present in a range of about 2 mg/L to about 50 mg/L, or, in other embodiments about 6 mg/L to about 40 mg/L. In still other embodiments, the gangliosides are present in a range of about 9 mg/L to about 35 mg/L. In some embodiments, total phospholipids in the nutritional composition (again not including phospholipids from plant sources such as soy lecithin) is in a range of about 6 mg/100 Kcal to about 300 mg/100 Kcal; in some embodiments it is about 12 mg/100 Kcal to about 150 mg/100 Kcal, or about 18 mg/100 Kcal to about 85 mg/100 Kcal. In certain embodiments, the buttermilk also contributes sphingomyelin in a range of about 1 mg/100 Kcal to about 60 mg/100 Kcal; in other embodiments, it is about 3.5 mg/100 Kcal to about 48 mg/100 Kcal, or about 6 mg/100 Kcal to about 30 mg/100 Kcal. And, gangliosides can be present in a range of about 0.25 mg/100 Kcal to about 7.5 mg/100 Kcal, or, in other embodiments about 0.7 mg/100 Kcal to about 6 mg/100 Kcal. In still other embodiments, the gangliosides are present in a range of about 1.1 mg/100 Kcal to about 5.3 mg/100 Kcal.

In certain embodiments, the nutritional composition includes an enriched lipid fraction, which may provide a source of saturated fatty acids, monounsaturated fatty acids, polyunsaturated fatty acids, OBCFAs, BCFAs, CLA, cholesterol, phospholipids to the nutritional composition, in addition to the buttermilk and its components.

Additionally, the enriched lipid fraction may comprise, in some embodiments, lauric acid. Lauric acid, also known as dodecanoic acid, is a saturated fatty acid with a 12-carbon atom chain and is believed to be one of the main antiviral and antibacterial substances currently found in human breast milk. Without being bound by any particular theory, it is believed that when the enriched lipid fraction is ingested, the mouth lingual lipase and pancreatic lipase will hydrolyze the triglycerides to a mixture of glycerides including monolauric and free lauric acid, which may be present in some embodiments at from 80 mg/100 ml to 800 mg/100 ml. The concentration of monolauryl can be in the range of 20 mg/100 ml to 300 mg/100 ml.

In some embodiments the enriched lipid fraction may also contain OBCFAs. In certain embodiments, the OBCFAs may be present in an amount from about 0.3 g/100 Kcal to about 6.1 g/100 Kcal. In other embodiments OBCFAs may be present in an amount from about 2.2 g/100 Kcal to about 4.3 g/100 Kcal. In yet another embodiment OBCFAs may be present in an amount from about 3.5 g/100 Kcal to about 5.7 g/100 Kcal.

In some embodiments, the enriched lipid fraction may comprise BCFAs. In some embodiments the BCFAs are present at a concentration from about 0.2 g/100 Kcal and about 5.82 g/100 Kcal. In another embodiment, the BCFAs are present in an amount of from about 2.3 g/100 Kcal to about 4.2 g/100 Kcal. In yet another embodiment the BCFAs are present from about 4.2 g/100 Kcal to about 5.82 g/100 Kcal.

The enriched lipid fraction may comprise CLA in some embodiments. CLA may be present in a concentration from about 0.4 g/100 Kcal to about 2.5 g/100 Kcal. In other embodiments CLA may be present from about 0.8 g/100 Kcal to about 1.2 g/100 Kcal. In yet other embodiments CLA may be present from about 1.2 g/100 Kcal to about 2.3 g/100 Kcal. Examples of CLAs found in the enriched lipid fraction for the nutritional composition include, but are not limited to, cis-9, trans-11 CLA, trans-10, cis-12 CLA, cis-9, trans-12 octadecadienoic acid, and mixtures thereof.

The nutritional composition of the disclosure also contains a source of LCPUFAs; especially a source of LCPUFAs that comprises DHA. Other suitable LCPUFAs include, but are not limited to, α-linoleic acid, γ-linoleic acid, linoleic acid, linolenic acid, eicosapentaenoic acid (EPA) and ARA.

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The amount of long chain polyunsaturated fatty acid in the nutritional composition is advantageously at least about 5 mg/100 Kcal, and may vary in some embodiments from about 24 mg/100 Kcal to about 90 mg/100 Kcal, more preferably from about 26 mg/100 Kcal to about 72 mg/100 Kcal. In certain embodiments, the LCPUFAs are present at a level of about 29 mg/100 Kcal to about 72 mg/100 Kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

The nutritional composition also contains one or more prebiotics (also referred to as a prebiotic component) in certain embodiments. Prebiotics exert health benefits, which may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose (PDX), polydextrose powder, lactulose, lactosucrose, raffinose, gluco-oligosaccharide, inulin, fructo-oligosaccharide (FOS), isomalto-oligosaccharide, soybean oligosaccharides, lactosucrose, xylo-oligosaccharide (XOS), chito-oligosaccharide, manno-oligosaccharide, aribino-oligosaccharide, siallyl-oligosaccharide, fuco-oligosaccharide, galacto-oligosaccharides (GOS) and gentio-oligosaccharides.

In an embodiment, the total amount of prebiotics present in the nutritional composition may be from about 1.0 g/L to about 10.0 g/L of the composition. More preferably, the total amount of prebiotics present in the nutritional composition may be from about 2.0 g/L and about 8.0 g/L of the composition. In some embodiments, the total amount of prebiotics present in the nutritional composition may be from about 0.01 g/100 Kcal to about 1.5 g/100 Kcal. In certain embodiments, the total amount of prebiotics present in the nutritional composition may be from about 0.15 g/100 Kcal to about 1.5 g/100 Kcal. Moreover, the nutritional composition may comprise a prebiotic component comprising PDX. In some embodiments, the prebiotic component comprises at least 20% w/w PDX, GOS or a mixture thereof.

The amount of PDX in the nutritional composition may, in an embodiment, be within the range of from about 0.015 g/100 Kcal to about 1.5 g/100 Kcal. In another embodiment, the amount of polydextrose is within the range of from about 0.2 g/100 Kcal to about 0.6 g/100 Kcal. In some embodiments, PDX may be included in the nutritional composition in an amount sufficient to provide between about 1.0 g/L and 10.0 g/L. In another embodiment, the nutritional composition contains an amount of PDX that is between about 2.0 g/L and 8.0 g/L. And in still other embodiments, the amount of PDX in the nutritional composition may be from about 0.05 g/100 Kcal to about 1.5 g/100 Kcal. In another embodiment, PDX is present in the nutritional composition at a level of from about 0.05 g/100 Kcal to about 1.3 g/100 Kcal.

The prebiotic component also comprises GOS in some embodiments. The amount of GOS in the nutritional composition may, in an embodiment, be from about 0.015 g/100 Kcal to about 1.0 g/100 Kcal. In another embodiment, the amount of GOS in the nutritional composition may be from about 0.2 g/100 Kcal to about 0.5 g/100 Kcal.

In a particular embodiment of the present disclosure, PDX is administered in combination with GOS.

In a particular embodiment, GOS and PDX are supplemented into the nutritional composition in a total amount of at least about 0.015 g/100 Kcal or about 0.015 g/100 Kcal to about 1.5 g/100 Kcal. In some embodiments, the nutritional composition may comprise GOS and PDX in a total amount of from about 0.1 to about 1.5 g/100 Kcal.

As noted, in some embodiments, the nutritional composition of the present disclosure includes sialic acid, short chain fatty acids and/or vitamin B12 in addition to the buttermilk, long chain polyunsaturated fatty acids, and prebiotics.

The term sialic acid (SA) is used to generally refer to a family of derivatives of neuraminic acid. N-acetylneuraminic acid (Neu5Ac) and N-glycolylneuraminic acid (Neu5Gc) are among the most abundant naturally found forms of SA, especially Neu5Ac in human and cow's milk. Mammalian brain tissue contains the highest levels of SA because of its incorporation into brain-specific proteins such as neural cell adhesion molecule (NCAM) and lipids (e.g., gangliosides). It is considered that SA plays a role in neural development and function, learning, cognition, and memory throughout the life. In human milk, SA exists as free and bound forms with oligosaccharides, protein and lipid. The content of SA in human milk varies with lactation stage, with the highest level found in colostrum. However, most SA in bovine milk is bound with proteins, compared to the majority of SA in human milk bound to free oligosaccharides. Sialic acid can be incorporated in to the disclosed nutritional composition as is, or it can be provided by incorporating casein glycomacropeptide (cGMP) having enhanced sialic acid content, as discussed in U.S. Pat. Nos. 7,867,541 and 7,951,410, the disclosure of each of which are incorporated by reference herein.

When present, sialic acid can be incorporated into the nutritional composition of the present disclosure at a level of about 100 mg/L to about 800 mg/L, including both inherent sialic acid from the buttermilk and exogenous sialic acid and sialic acid from sources such as cGMP. In some embodiments, sialic acid is present at a level of about 120 mg/L to about 600 mg/L; in other embodiments the level is about 140 mg/L to about 500 mg/L. In certain embodiments, sialic acid may be present in an amount from about 1 mg/100 Kcals to about 120 mg/100 Kcal. In other embodiments sialic acid may be present in an amount from about 14 mg/100 Kcal to about 90 mg/100 Kcal. In yet other embodiments, sialic acid may be present in an amount from about 15 mg/100 Kcal to about 75 mg/100 Kcal.

In some embodiments the nutritional composition contains short chain fatty acids (i.e., fatty acids having a chain length of 6 carbons or less). The short chain fatty acids may be present in a concentration from about 2 mg/100 Kcal to about 200 mg/100 Kcal. In certain embodiments the short chain fatty acids may be present from about 5 mg/100 Kcal to about 150 mg/100 Kcal. In still other embodiments the short chain fatty acids may be present from about 8 mg/100 Kcal to about 100 mg/100 Kcal. Examples of short chain fatty acids suitable for inclusion include, but are not limited to, acetic, propionic, butyric, isobutyric, valeric, isovaleric, caproic, and/or combinations thereof, with butyric acid and caproic acid being preferred. The ratio of short chain fatty acids (especially butyric acid and caproic acid) to the LCPUFAs is, in some embodiments, in the range of 1:10 to 10:1.

Vitamin B12 (cobalamin) is exclusively produced by bacteria, and humans are dependent on nutritional intake of B12 from dietary sources. In infants, severe B12 deficiency produces neurological symptoms such as irritability, anorexia, apathy and development regression. While not fully clear, the mechanisms may relate to delayed myelination or demyelination of nerves. Haptocorrin as a B12 binding protein is found in human milk. Haptocorrin therefore likely facilitates the uptake of vitamin B12. There is less information related to haptocorrin in cow's milk based infant formula. But, vitamin B12 is not stable at acid condition such as in stomach. However, it was found that its stability in a complex of B12 and lactoferrin was improved. In certain embodiments, therefore, vitamin B12 is provided with, or associated with, lactoferrin, wherein the Vitamin B12 is present in a range of about 0.018 mcg/100 Kcal to about 1.5 mcg/100 Kcal; in other embodiments, the vitamin B12 level is about 0.045 mcg/100 Kcal to about 1.4 mcg/100 Kcal, or even about 0.15 mcg/100 Kcal to about 1.2 mcg/100 Kcal.

In addition, in some embodiments, lactoferrin is also included in the nutritional composition of the present disclosure. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms. For instance, the N-terminal residues 1-47 of human lactoferrin (1-48 of bovine lactoferrin) are critical to the iron-independent biological activities of lactoferrin. In human lactoferrin, residues 2 to 5 (RRRR) and 28 to 31 (RKVR) are arginine-rich cationic domains in the N-terminus especially critical to the antimicrobial activities of lactoferrin. A similar region in the N-terminus is found in bovine lactoferrin (residues 17 to 42; FKCRRWQWRMKKLGAPSITCVRRAFA).

Lactoferrins from different host species may vary in their amino acid sequences though commonly possess a relatively high isoelectric point with positively charged amino acids at the end terminal region of the internal lobe. Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 55% homology with human lactoferrin and in some embodiments, at least 65% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin.

In one embodiment, lactoferrin is present in the nutritional composition in an amount of at least about 15 mg/100 Kcal. In certain embodiments, the nutritional composition may include between about 15 and about 300 mg lactoferrin per 100 Kcal. In another embodiment, where the nutritional composition is an infant formula, the nutritional composition may comprise lactoferrin in an amount of from about 60 mg to about 150 mg lactoferrin per 100 Kcal; in yet another embodiment, the nutritional composition may comprise about 60 mg to about 120 mg lactoferrin per 100 Kcal. In some embodiments, when the nutritional composition is liquid, it can include lactoferrin in the quantities of from about 0.3 g/L to about 18 g/L of composition. In nutritional compositions providing complete nutrition, lactoferrin may be present in quantities of from about 0.3 g/L to about 4.4 g/L. In certain embodiments, the nutritional composition may comprise between about 0.3 g/L and about 2.5 g/L. In some embodiments, the nutritional composition includes between about 0.4 and about 1.5 grams lactoferrin per liter of formula.

Lactoferrin for use in the present disclosure may be, for example, isolated from the milk of a non-human animal or produced by a genetically modified organism. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. EBA, also sometimes called stabilized fluid bed adsorption, is a process for isolating a milk protein, such as lactoferrin, from a milk source comprises establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof.

In particular embodiments, the target protein is lactoferrin, though other milk proteins, such as lactoperoxidases or lactalbumins, also may be isolated. In some embodiments, the process comprises the steps of establishing an expanded bed adsorption column comprising a particulate matrix, applying a milk source to the matrix, and eluting the lactoferrin from the matrix with about 0.3 to about 2.0M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046, the disclosures of which are hereby incorporated by reference herein. In some embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The isoelectric point of lactoferrin is approximately 8.9. Prior EBA methods of isolating lactoferrin use 200 mM sodium hydroxide as an elution buffer. Thus, the pH of the system rises to over 12, and the structure and bioactivity of lactoferrin may be comprised, by irreversible structural changes. It has now been discovered that a sodium chloride solution can be used as an elution buffer in the isolation of lactoferrin from the EBA matrix. In certain embodiments, the sodium chloride has a concentration of about 0.3 M to about 2.0 M. In other embodiments, the lactoferrin elution buffer has a sodium chloride concentration of about 0.3 M to about 1.5 M, or about 0.5 m to about 1.0 M.

In some embodiments, the nutritional composition(s) of the disclosure may also comprise at least one protein or protein equivalent source (other than lactoferrin and the buttermilk proteins), which can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In some embodiments, the proteins of the nutritional composition are provided as intact proteins. In other embodiments, the proteins are provided as a combination of both intact proteins and hydrolyzed proteins. In certain embodiments, the proteins may be partially hydrolyzed or extensively hydrolyzed. In still other embodiments, the protein equivalent source comprises amino acids. In yet another embodiment, the protein source may be supplemented with glutamine-containing peptides. In another embodiment, the protein component comprises extensively hydrolyzed protein. In still another embodiment, the protein component of the nutritional composition consists essentially of extensively hydrolyzed protein in order to minimize the occurrence of food allergy. In yet another embodiment, the protein source may be supplemented with glutamine-containing peptides.

Accordingly, in some embodiments, the protein component of the nutritional composition comprises either partially or extensively hydrolyzed protein, such as protein from cow's milk. The hydrolyzed proteins may be treated with enzymes to break down some or most of the proteins that cause adverse symptoms with the goal of reducing allergic reactions, intolerance, and sensitization. Moreover, the proteins may be hydrolyzed by any method known in the art.

The terms "protein hydrolysates" or "hydrolyzed protein" are used interchangeably herein and refer to hydrolyzed proteins, wherein the degree of hydrolysis is may be from about 2% to about 80%, or from 3% to 20%, or from 20% to 80%, or from about 30% to about 80%, or even from about 40% to about 60%.

When a peptide bond in a protein is broken by enzymatic hydrolysis, one amino group is released for each peptide bond broken, causing an increase in amino nitrogen. It should be noted that even non-hydrolyzed protein would contain some exposed amino groups. Hydrolyzed proteins will also have a different molecular weight distribution than the non-hydrolyzed proteins from which they were formed. The functional and nutritional properties of hydrolyzed proteins can be affected by the different size peptides. A molecular weight profile is usually given by listing the percent by weight of particular ranges of molecular weight (in Daltons) fractions (e.g., 2,000 to 5,000 Daltons, greater than 5,000 Daltons).

In a particular embodiment, the nutritional composition contains free amino acids as a protein equivalent source. In this embodiment, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In other embodiments, small amino acid peptides may be included as the protein component of the nutritional composition. Such small amino acid peptides may be naturally occurring or synthesized. The amount of free amino acids in the nutritional composition may vary from about 1 to about 5 g/100 Kcal. In an embodiment, 100% of the free amino acids have a molecular weight of less than 500 Daltons. In this embodiment, the nutritional formulation may be hypoallergenic.

In an embodiment, the protein source comprises from about 40% to about 85% whey protein and from about 15% to about 60% casein.

In some embodiments, the nutritional composition comprises no greater than 7 g/100 Kcal, and, in certain embodiments, between about 1 g and about 7 g of a protein and/or protein equivalent source per 100 Kcal. In other embodiments, the nutritional composition comprises between about 1.5 g and about 4.5 g of protein or protein equivalent per 100 Kcal.

In some embodiments, the nutritional composition comprises at least one carbohydrate source. Carbohydrate sources can be any used in the art, e.g., lactose, glucose, fructose, corn syrup solids, maltodextrins, sucrose, starch, rice syrup solids, and the like. The amount of the additional carbohydrate component in the nutritional composition typically can be greater than 5 g/100 Kcal; in some embodiments, it can vary from between about 5 g and about 25 g/100 Kcal. In some embodiments, the amount of carbohydrate is between about 6 g and about 22 g/100 Kcal. In other embodiments, the amount of carbohydrate is between about 9 g and about 14 g/100 Kcal. In some embodiments, corn syrup solids and/or maltodextrin are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

In one particular embodiment, the carbohydrate component of the nutritional composition is comprised of 100% lactose. In another embodiment, the additional carbohydrate component comprises between about 0% and 60% lactose. In another embodiment, the carbohydrate component comprises between about 15% and 55% lactose. In yet another embodiment, the carbohydrate component comprises between about 15% and 30% lactose. In these embodiments, the remaining source of carbohydrates may be any carbohydrate known in the art. In an embodiment, the carbohydrate component comprises about 25% lactose and about 75% corn syrup solids.

In some embodiments, the carbohydrate may comprise at least one starch or starch component. A starch is a carbohydrate composed of two distinct polymer fractions: amylose and amylopectin. Amylose is the linear fraction consisting of α-1,4 linked glucose units. Amylopectin has the same structure as amylose, but some of the glucose units are combined in an α-1,6 linkage, giving rise to a branched structure. Starches generally contain 17-24% amylose and from 76-83% amylopectin. Yet special genetic varieties of plants have been developed that produce starch with unusual amylose to amylopectin ratios. Some plants produce starch that is free of amylose. These mutants produce starch granules in the endosperm and pollen that stain red with iodine and that contain nearly 100% amylopectin. Predominant among such amylopectin producing plants are waxy corn, waxy sorghum, waxy potato, and waxy rice starch.

The performance of starches under conditions of heat, shear and acid may be modified or improved by physical or chemical modifications. Modifications are usually attained by introduction of substituent chemical groups. For example, viscosity at high temperatures or high shear can be increased or stabilized by cross-linking with di- or polyfunctional reagents, such as phosphorus oxychloride.

In some instances, the nutritional compositions of the present disclosure comprise at least one starch that is gelatinized or pregelatinized. As is known in the art, gelatinization occurs when polymer molecules interact over a portion of their length to form a network that entraps solvent and/or solute molecules. Moreover, if pectin is used, gels form when pectin molecules lose some water of hydration owing to competitive hydration of cosolute molecules. Factors that influence the occurrence of gelation include pH, concentration of cosolutes, concentration and type of cations, temperature and pectin concentration. Notably, LM pectin will gel only in the presence of divalent cations, such as calcium ions. And among LM pectins, those with the lowest degree of esterification have the highest gelling temperatures and the greatest need for divalent cations for crossbridging.

Meanwhile, pregelatinization of starch is a process of precooking starch to produce material that hydrates and swells in cold water. The precooked starch is then dried, for example by drum drying or spray drying. Moreover the starch of the present disclosure can be chemically modified to further extend the range of its finished properties. The nutritional compositions of the present disclosure may comprise at least one pregelatinized starch.

Native starch granules are insoluble in water, but, when heated in water, native starch granules begin to swell when sufficient heat energy is present to overcome the bonding forces of the starch molecules. With continued heating, the granule swells to many times its original volume. The friction between these swollen granules is the major factor that contributes to starch paste viscosity.

The nutritional composition of the present disclosure may comprise native or modified starches, such as, for example, waxy corn starch, waxy rice starch, corn starch, rice starch, potato starch, tapioca starch, wheat starch or any mixture thereof. Generally, common corn starch comprises about 25% amylose, while waxy corn starch is almost totally made up of amylopectin. Meanwhile, potato starch generally comprises about 20% amylose and 80% amylopectin, rice starch comprises an similar amylose:amylopectin ratio, and waxy rice starch comprises only about 2% amylose. Further, tapioca starch generally comprises about 15% to about 18% amylose, and wheat starch has an amylose content of around 25%, the rest is amylopectin.

In some embodiments, the nutritional composition comprises gelatinized and/or pre-gelatinized waxy corn starch. In other embodiments, the nutritional composition comprises gelatinized and/or pre-gelatinized tapioca starch. Other gelatinized or pre-gelatinized starches, such as rice starch or potato starch may also be used.

Additionally, the nutritional compositions of the present disclosure can comprise at least one source of pectin in some embodiments. The source of pectin may comprise any variety or grade of pectin known in the art. In some embodiments, the pectin has a degree of esterification of less than 50% and is classified as low methylated ("LM") pectin. In some embodiments, the pectin has a degree of esterification of greater than or equal to 50% and is classified as high-ester or high methylated ("HM") pectin. In still other embodiments, the pectin is very low ("VL") pectin, which has a degree of esterification that is less than approximately 15%. Further, the nutritional composition of the present disclosure may comprise LM pectin, HM pectin, VL pectin, or any mixture thereof. The nutritional composition may include pectin that is soluble in water. And, as known in the art, the solubility and viscosity of a pectin solution are related to the molecular weight, degree of esterification, concentration of the pectin preparation and the pH and presence of counterions.

Moreover, pectin has a unique ability to form gels. Generally, under similar conditions, a pectin's degree of gelitization, the gelling temperature, and the gel strength are proportional to one another, and each is generally proportional to the molecular weight of the pectin and inversely proportional to the degree of esterification. For example, as the pH of a pectin solution is lowered, ionization of the carboxylate groups is repressed, and, as a result of losing their charge, saccharide molecules do not repel each other over their entire length. Accordingly, the polysaccharide molecules can associate over a portion of their length to form a gel. Yet pectins with increasing degrees of methylation will gel at somewhat higher pH because they have fewer carboxylate anions at any given pH.

The nutritional composition may comprise a gelatinized and/or pregelatinized starch together with pectin and/or gelatinized pectin. While not wishing to be bound by this or any other theory, it is believed that the use of pectin, such as LM pectin, which is a hydrocolloid of large molecular weight, together with starch granules, provides a synergistic effect that increases the molecular internal friction within a fluid matrix. The carboxylic groups of the pectin may also interact with calcium ions present in the nutritional composition, thus leading to an increase in viscosity, as the carboxylic groups of the pectin form a weak gel structure with the calcium ion(s), and also with peptides present in the nutritional composition. In some embodiments, the nutritional composition comprises a ratio of starch to pectin that is between about 12:1 and 20:1, respectively. In other embodiments, the ratio of starch to pectin is about 17:1. In some embodiments, the nutritional composition may comprise between about 0.05 and about 2.0% w/w pectin. In a particular embodiment, the nutritional composition may comprise about 0.5% w/w pectin.

Pectins for use herein typically have a peak molecular weight of 8,000 Daltons or greater. The pectins of the present disclosure have a preferred peak molecular weight of between 8,000 and about 500,000, more preferred is between about 10,000 and about 200,000 and most preferred is between about 15,000 and about 100,000 Daltons. In some embodiments, the pectin of the present disclosure may be hydrolyzed pectin. In certain embodiments, the nutritional composition comprises hydrolyzed pectin having a molecular weight less than that of intact or unmodified pectin. The hydrolyzed pectin of the present disclosure can be prepared by any means known in the art to reduce molecular weight. Examples of said means are chemical hydrolysis, enzymatic hydrolysis and mechanical shear. A preferred means of reducing the molecular weight is by alkaline or neutral hydrolysis at elevated temperature. In some embodiments, the nutritional composition comprises partially hydrolyzed pectin. In certain embodiments, the partially hydrolyzed pectin has a molecular weight that is less than that of intact or unmodified pectin but more than 3,300 Daltons.

The nutritional composition may contain at least one acidic polysaccharide. An acidic polysaccharide, such as negatively charged pectin, may induce an anti-adhesive effect on pathogens in a subject's gastrointestinal tract. Indeed, nonhuman milk acidic oligosaccharides derived from pectin are able to interact with the epithelial surface and are known to inhibit the adhesion of pathogens on the epithelial surface.

In some embodiments, the nutritional composition comprises at least one pectin-derived acidic oligosaccharide. Pectin-derived acidic oligosaccharide(s) (pAOS) result from enzymatic pectinolysis, and the size of a pAOS depends on the enzyme use and on the duration of the reaction. In such embodiments, the pAOS may beneficially affect a subject's stool viscosity, stool frequency, stool pH and/or feeding tolerance. The nutritional composition of the present disclosure may comprise between about 2 g pAOS per liter of formula and about 6 g pAOS per liter of formula. In an embodiment, the nutritional composition comprises about 0.2 g pAOS/dL, corresponding to the concentration of acidic oligosaccharides in human milk. (Fanaro et al., "Acidic Oligosaccharides from Pectin Hydrolysate as New Component for Infant Formulae: Effect on Intestinal Flora, Stool Characteristics, and pH", Journal of Pediatric Gastroenterology and Nutrition, 41: 186-190, August 2005)

In some embodiments, the nutritional composition comprises up to about 20% w/w of a mixture of starch and pectin. In some embodiments, the nutritional composition comprises up to about 19% starch and up to about 1% pectin. In other embodiments, the nutritional composition comprises about up to about 15% starch and up to about 5% pectin. In still other embodiments, the nutritional composition comprises up to about 18% starch and up to about 2% pectin. In some embodiments the nutritional composition comprises between about 0.05% w/w and about 20% w/w of a mixture of starch and pectin. Other embodiments include between about 0.05% and about 19% w/w starch and between about 0.05% and about 1% w/w pectin. Further, the nutritional composition may comprise between about 0.05% and about 15% w/w starch and between about 0.05% and about 5% w/w pectin.

Suitable fats or lipids for use in the nutritional composition of the present disclosure may be any known or used in the art, including but not limited to, animal sources, e.g., milk fat, cream, butter, butter fat, egg yolk lipid; marine sources, such as fish oils, marine oils, single cell oils; vegetable and plant oils, such as corn oil, canola oil, sunflower oil, soybean oil, palmolein, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils, structured lipids (e.g., Infat® manufactured from Advanced Lipids, and Betapol® provided from Loders Croklaan. Both are palmitic acid enriched in sn-2 position of triglycerides) and emulsions and esters of fatty acids; and any combinations thereof.

The amount of lipids or fats is, in one embodiment, no greater than about 7 g/100 Kcal; in some embodiments, the lipid or fat is present at a level of from about 2 to about 7 g/100 Kcal.

It has been found that nutritional supplementation of inositol represents a feasible and effective approach to promote oligodendrocyte survival and proliferation in a dose dependent manner, resulting in a consistent increase in the number of oligodendrocyte precursor cells. Nutritional supplementation with inositol provides benefits for enhanced developmental myelination by which it translates into a fundamental benefit for brain development. Given the importance of functional myelination, nutritional supplementation of inositol is beneficial to pediatric subjects by enhancing brain development and health. Moreover, the sweet taste of inositol provides further advantages in terms of palatability to pediatric consumers.

As such, in certain embodiments, inositol is present in the nutritional compositions of the present disclosure at a level of at least about 4 mg/100 Kcal; in other embodiments, inositol should be present at a level of no greater than about 70 mg/100 Kcal. In still other embodiments, the nutritional composition comprises inositol at a level of about 5 mg/100 Kcal to about 65 mg/100 Kcal. In a further embodiment, inositol is present in the nutritional composition at a level of about 7 mg/100 Kcal to about 50 mg/100 Kcal. Moreover, inositol can be present as exogenous inositol or inherent inositol. In embodiments, a major fraction of the inositol (i.e., at least 40%) is exogenous inositol. In certain embodiments, the ratio of exogenous to inherent inositol is at least 50:50; in other embodiments, the ratio of exogenous to inherent inositol is at least 60:40.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (LGG) (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140), a spore-former such as *Bacillus coagulans* (ATCC PTA-6086, 6085, 6087, 11748), or any combination thereof.

If included in the composition, the amount of the probiotic may vary from about $1\times10^4$ to about $1.5\times10^{12}$ cfu of probiotic(s) per 100 Kcal. In some embodiments the amount of probiotic may be from about $1\times10^6$ to about $1\times10^9$ cfu of probiotic(s) per 100 Kcal. In certain other embodiments the amount of probiotic may vary from about $1\times10^7$ cfu/100 Kcal to about $1\times10^8$ cfu of probiotic(s) per 100 Kcal.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

In some embodiments, the nutritional composition may include a source comprising probiotic cell equivalents, which refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc. In non-viable probiotics are included in the nutritional composition, the amount of the probiotic cell equivalents may vary from about $1\times10^4$ to about $1.5\times10^{10}$ cell equivalents of probiotic(s) per 100 Kcal. In some embodiments the amount of probiotic cell equivalents may be from about $1\times10^6$ to about $1\times10^9$ cell equivalents of probiotic(s) per 100 Kcal nutritional composition. In certain other embodiments the amount of probiotic cell equivalents may vary from about $1\times10^7$ to about $1\times10^8$ cell equivalents of probiotic(s) per 100 Kcal of nutritional composition.

In some embodiments, the probiotic source incorporated into the nutritional composition may comprise both viable colony-forming units, and non-viable cell-equivalents.

In some embodiments, the nutritional composition includes a culture supernatant from a late-exponential growth phase of a probiotic batch-cultivation process. Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In some embodiments, the culture supernatant is harvested at a point in time of 75% to 85% of the duration of the exponential phase, and may be harvested at about ⅘ of the time elapsed in the exponential phase.

The disclosed nutritional composition may also comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalities, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, Saccharomyces cerevisiae, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

The nutritional composition of the present disclosure comprises β-glucan. In some embodiments, the β-glucan is β-1,3;1,6-glucan. In some embodiments, the β-1,3;1,6-glucan is derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

In some embodiments, the amount of β-glucan present in the composition is at between about 0.010 and about 0.080 g per 100 g of composition. In other embodiments, the nutritional composition comprises between about 4 and about 35 mg β-glucan per serving. In another embodiment, the nutritional composition comprises between about 5 and about 30 mg β-glucan per 8 fl. oz. (236.6 mL) serving. In other embodiments, the nutritional composition comprises an amount of β-glucan sufficient to provide between about 15 mg and about 90 mg 3-glucan per day. The nutritional composition may be delivered in multiple doses to reach a target amount of β-glucan delivered to the subject throughout the day.

In some embodiments, the amount of β-glucan in the nutritional composition is between about 2.5 mg and about 17 mg per 100 Kcal. In another embodiment the amount of β-glucan is between about 4 mg and about 17 mg per 100 Kcal.

One or more additional vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

The nutritional composition may optionally include one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E (α-tocopherol, α-tocopherol acetate, α-tocopherol succinate, α-tocopherol nicotinate, α-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof.

Further, the nutritional composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional compositions of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), sodium caseinate, alpha lactalbumin and/or mono- and di-glycerides, pectin, octenyl succinic anhydride (OSA) modified starch, OSA modified maltodextrin, OSA modified pectin and their derivatives and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 μm, more preferably in the range of 10 μm to 400 μm.

If the nutritional composition is in the form of a ready-to-use product, the osmolality of the nutritional composition may be between about 100 and about 1100 mOsm/kg water, more typically about 200 to about 700 mOsm/kg water.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 1 to about 7 g/100 Kcal. The amount of protein typically can vary from about 1 to about 7 g/100 Kcal. The amount of carbohydrate typically can vary from about 6 to about 22 g/100 Kcal.

The nutritional composition of the present disclosure may further include at least one additional phytonutrient. Phytonutrients, or their derivatives, conjugated forms or precursors, that are identified in human milk are preferred for inclusion in the nutritional composition. Typically, dietary sources of carotenoids and polyphenols are absorbed by a nursing mother and retained in milk, making them available to nursing infants. Addition of these phytonutrients to infant or children's formulas allows such formulas to mirror the composition and functionality of human milk and to promote general health and well being.

For example, in some embodiments, the nutritional composition of the present disclosure may comprise, in an 8 fl. oz. (236.6 mL) serving, between about 80 and about 300 mg anthocyanins, between about 100 and about 600 mg proanthocyanidins, between about 50 and about 500 mg flavan-3-ols, or any combination or mixture thereof. In other embodiments, the nutritional composition comprises apple extract, grape seed extract, or a combination or mixture thereof. Further, the at least one phytonutrient of the nutritional composition may be derived from any single or blend of fruit, grape seed and/or apple or tea extract(s).

For the purposes of this disclosure, additional phytonutrients may be added to a nutritional composition in native, purified, encapsulated and/or chemically or enzymatically-modified form so as to deliver the desired sensory and stability properties. In the case of encapsulation, it is desirable that the encapsulated phytonutrients resist dissolution with water but are released upon reaching the small intestine. This could be achieved by the application of enteric coatings, such as cross-linked alginate and others.

Examples of additional phytonutrients suitable for the nutritional composition include, but are not limited to, anthocyanins, proanthocyanidins, flavan-3-ols (i.e. catechins, epicatechins, etc.), flavanones, flavonoids, isoflavonoids, stilbenoids (i.e. resveratrol, etc.) proanthocyanidins, anthocyanins, resveratrol, quercetin, curcumin, and/or any mixture thereof, as well as any possible combination of phytonutrients in a purified or natural form. Certain components, especially plant-based components of the nutritional compositions may provide a source of phytonutrients.

Some amounts of phytonutrients may be inherently present in known ingredients, such as natural oils, that are commonly used to make nutritional compositions for pediatric subjects. These inherent phytonutrient(s) may be but are not necessarily considered part of the phytonutrient component described in the present disclosure. In some embodiments, the phytonutrient concentrations and ratios as described herein are calculated based upon added and inherent phytonutrient sources. In other embodiments, the phytonutrient concentrations and ratios as described herein are calculated based only upon added phytonutrient sources.

In some embodiments, the nutritional composition comprises anthocyanins, such as, for example, glucosides of aurantinidin, cyanidin, delphinidin, europinidin, luteolinidin, pelargonidin, malvidin, peonidin, petunidin, and rosinidin. These and other anthocyanins suitable for use in the nutritional composition are found in a variety of plant sources. Anthocyanins may be derived from a single plant source or a combination of plant sources. Non-limiting examples of plants rich in anthocyanins suitable for use in the inventive composition include: berries (acai, grape, bilberry, blueberry, lingonberry, black currant, chokeberry, blackberry, raspberry, cherry, red currant, cranberry, crowberry, cloudberry, whortleberry, rowanberry), purple corn, purple potato, purple carrot, red sweet potato, red cabbage, eggplant.

In some embodiments, the nutritional composition of the present disclosure comprises proanthocyanidins, which include but are not limited to flavan-3-ols and polymers of flavan-3-ols (e.g., catechins, epicatechins) with degrees of polymerization in the range of 2 to 11. Such compounds may be derived from a single plant source or a combination of plant sources. Non-limiting examples of plant sources rich in proanthocyanidins suitable for use in the disclosed nutritional composition include: grape, grape skin, grape seed, green tea, black tea, apple, pine bark, cinnamon, cocoa, bilberry, cranberry, black currant chokeberry.

Non-limiting examples of flavan-3-ols which are suitable for use in the disclosed nutritional composition include catechin, epicatechin, gallocatechin, epigallocatechin, epicatechin gallate, epicatechin-3-gallate, epigallocatechin and gallate. Plants rich in the suitable flavan-3-ols include, but are not limited to, teas, red grapes, cocoa, green tea, apricot and apple.

Certain polyphenol compounds, in particular flavan-3-ols, may improve learning and memory in a human subject by increasing brain blood flow, which is associated with an increase and sustained brain energy/nutrient delivery as well as formation of new neurons. Polyphenols may also provide neuroprotective actions and may increase both brain synaptogenesis and antioxidant capability, thereby supporting optimal brain development in younger children. Polyphenol compounds, in particular flavan-3-ols form complexes with proteins, such as caseins. This complex formation provides them additional protection from oxidation through the gastrointestinal track. This complex formation may also be with digestive enzymes, such as carbohydrases, thus inducing a longer period of carbohydrate hydrolysis, that is glucose release, hence providing a sustained energy profile.

Preferred sources of flavan-3-ols for the nutritional composition include green tea, black tea, as well as extacts and mixtures thereof. Other preferred sources of flavan-3-ols include at least one apple extract, at least one grape seed extract or a mixture thereof. For apple extracts, flavan-3-ols are broken down into monomers occurring in the range 4% to 20% and polymers in the range 80% to 96%. For grape seed extracts flavan-3-ols are broken down into monomers (about 46%) and polymers (about 54%) of the total flavan-3-ols and total polyphenolic content. Preferred degree of polymerization of polymeric flavan-3-ols is in the range of between about 2 and 11. Furthermore, apple and grape seed extracts may contain catechin, epicatechin, epigallocatechin, epicatechin gallate, epigallocatechin gallate, polymeric proanthocyanidins, stilbenoids (i.e. resveratrol), flavonols (i.e. quercetin, myricetin), or any mixture thereof. Plant sources rich in flavan-3-ols include, but are not limited to apple, grape seed, grape, grape skin, tea (green or black), pine bark, cinnamon, cocoa, bilberry, cranberry, black currant, chokeberry.

An amount of flavan-3-ols, including monomeric flavan-3-ols, polymeric flavan-3-ols or a combination thereof, ranging from between about 0.01 mg and about 450 mg per day may be administered. In some cases, the amount of flavan-3-ols administered to an infant or child may range from about 0.01 mg to about 170 mg per day, from about 50 to about 450 mg per day, or from about 100 mg to about 300 mg per day.

In an embodiment of the disclosure, flavan-3-ols are present in the nutritional composition in an amount ranging from about 0.4 to about 3.8 mg/g nutritional composition (about 9 to about 90 mg/100 Kcal). In another embodiment, flavan-3-ols are present in an amount ranging from about 0.8 to about 2.5 mg/g nutritional composition (about 20 to about 60 mg/100 Kcal).

In some embodiments, the nutritional composition of the present disclosure comprises flavanones. Non-limiting examples of suitable flavanones include butin, eriodictyol, hesperetin, hesperidin, homeriodictyol, isosakuranetin, naringenin, naringin, pinocembrin, poncirin, sakuranetin, sakuranin, steurbin. Plant sources rich in flavanones include, but are not limited to orange, tangerine, grapefruit, lemon, lime. The nutritional composition may be formulated to deliver between about 0.01 and about 150 mg flavanones per day.

Moreover, the nutritional composition may also comprise flavonols. Flavonols from plant or algae extracts may be used. Flavonols, such as ishrhametin, kaempferol, myricetin, quercetin, may be included in the nutritional composition in amounts sufficient to deliver between about 0.01 and 150 mg per day to a subject.

The phytonutrient component of the nutritional composition may also comprise phytonutrients that have been identified in human milk, including but not limited to naringenin, hesperetin, anthocyanins, quercetin, kaempferol, epicatechin, epigallocatechin, epicatechin-gallate, epigallocatechin-gallate or any combination thereof. In certain embodiments, the nutritional composition comprises between about 50 and about 2000 nmol/L epicatechin, between about 40 and about 2000 nmol/L epicatechin gallate, between about 100 and about 4000 nmol/L epigallocatechin gallate, between about 50 and about 2000 nmol/L naringenin, between about 5 and about 500 nmol/L kaempferol, between about 40 and about 4000 nmol/L hesperetin, between about 25 and about 2000 nmol/L anthocyanins, between about 25 and about 500 nmol/L quercetin, or a mixture thereof. Furthermore, the nutritional composition may comprise the metabolite(s) of a phytonutrient or of its parent compound, or it may comprise other classes of dietary phytonutrients, such as glucosinolate or sulforaphane.

In certain embodiments, the nutritional composition comprises carotenoids, such as lutein, zeaxanthin, astaxanthin, lycopene, beta-carotene, alpha-carotene, gamma-carotene, and/or beta-cryptoxanthin. Plant sources rich in carotenoids include, but are not limited to kiwi, grapes, citrus, tomatoes, watermelons, papayas and other red fruits, or dark greens, such as kale, spinach, turnip greens, collard greens, romaine lettuce, broccoli, zucchini, garden peas and Brussels sprouts, spinach, carrots.

Humans cannot synthesize carotenoids, but over 34 carotenoids have been identified in human breast milk, including isomers and metabolites of certain carotenoids. In addition to their presence in breast milk, dietary carotenoids, such as alpha and beta-carotene, lycopene, lutein, zeaxanthin, astaxanthin, and cryptoxanthin are present in serum of lactating women and breastfed infants. Carotenoids in general have been reported to improve cell-to-cell communication, promote immune function, support healthy respiratory health, protect skin from UV light damage, and have been linked to reduced risk of certain types of cancer, and all-cause mortality. Furthermore, dietary sources of carotenoids and/or polyphenols are absorbed by human subjects, accumulated and retained in breast milk, making them available to nursing infants. Thus, addition of phytonutrients to infant formulas or children's products would bring the formulas closer in composition and functionality to human milk.

Flavonoids, as a whole, may also be included in the nutritional composition, as flavonoids cannot be synthesized by humans. Moreover, flavonoids from plant or algae extracts may be useful in the monomer, dimer and/or polymer forms. In some embodiments, the nutritional composition comprises levels of the monomeric forms of flavonoids similar to those in human milk during the first three months of lactation. Although flavonoid aglycones (monomers) have been identified in human milk samples, the conjugated forms of flavonoids and/or their metabolites may also be useful in the nutritional composition. The flavonoids could be added in the following forms: free, glucuronides, methyl glucuronides, sulphates, and methyl sulphates.

The nutritional composition may also comprise isoflavonoids and/or isoflavones. Examples include, but are not limited to, genistein (genistin), daidzein (daidzin), glycitein, biochanin A, formononetin, coumestrol, irilone, orobol, pseudobaptigenin, anagyroidisoflavone A and B, calycosin, glycitein, irigenin, 5-O-methylgenistein, pratensein, prunetin, psi-tectorigenin, retusin, tectorigenin, iridin, ononin, puerarin, tectoridin, derrubone, luteone, wighteone, alpinumisoflavone, barbigerone, di-O-methylalpinumisoflavone, and 4'-methyl-alpinumisoflavone. Plant sources rich in isoflavonoids, include, but are not limited to, soybeans, psoralea, kudzu, lupine, fava, chick pea, alfalfa, legumes and peanuts. The nutritional composition may be formulated to deliver between about 0.01 and about 150 mg isoflavones and/or isoflavonoids per day.

In an embodiment, the nutritional composition(s) of the present disclosure comprises an effective amount of choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes an effective amount of choline, which is about 20 mg choline per 8 fl. oz. (236.6 mL) serving to about 100 mg per 8 fl. oz. (236.6 mL) serving.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The present disclosure further provides a method for providing nutritional support to a subject. The method includes administering to the subject an effective amount of the nutritional composition of the present disclosure.

The nutritional composition may be expelled directly into a subject's intestinal tract. In some embodiments, the nutritional composition is expelled directly into the gut. In some embodiments, the composition may be formulated to be consumed or administered enterally under the supervision of a physician and may be intended for the specific dietary management of a disease or condition, such as celiac disease and/or food allergy, for which distinctive nutritional requirements, based on recognized scientific principles, are established by medical evaluation.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

In some embodiments, the nutritional composition may be delivered to an infant from birth until a time that matches full-term gestation. In some embodiments, the nutritional composition may be delivered to an infant until at least about three months corrected age. In another embodiment, the nutritional composition may be delivered to a subject as long as is necessary to correct nutritional deficiencies. In yet another embodiment, the nutritional composition may be delivered to an infant from birth until at least about six months corrected age. In yet another embodiment, the nutritional composition may be delivered to an infant from birth until at least about one year corrected age.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

In certain embodiments, the nutritional composition is hypoallergenic. In other embodiments, the nutritional composition is kosher and/or halal. In still further embodiments, the nutritional composition is a non-genetically modified product. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

In some embodiments, the disclosure is directed to a staged nutritional feeding regimen for a pediatric subject, such as an infant or child, which includes a plurality of different nutritional compositions according to the present disclosure. The nutritional compositions described herein may be administered once per day or via several administrations throughout the course of a day.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

Example 1

An exemplary formulation in accordance with the present disclosure is as follows:

| Nutrient | Unit | Per 100 Kcal |
|---|---|---|
| Protein | g | 2.1 |
| Fat | g | 5.3 |
| Buttermilk | g | 3.5 |
| Linoleic Acid | mg | 810 |
| Alpha-Linolenic Acid | mg | 71 |
| Docosahexaenoic Acid | mg | 17.8 |
| Arachidonic Acid | mg | 36 |
| Carbohydrates | g | 11.2 |
| GOS | g | 0.31 |
| Polydextrose | g | 0.31 |
| Vitamin A | µg | 84 |
| Vitamin D | µg | 1.55 |
| Vitamin E | mg | 1.27 |
| Vitamin K | µg | 7.2 |
| Thiamin | µg | 85 |
| Riboflavin | µg | 170 |
| Vitamin B6 | µg | 60 |
| Vitamin B12 | µg | 0.31 |
| Niacin | µg | 660 |
| Folic Acid | µg | 18 |
| Pantothenic Acid | µg | 570 |
| Biotin | µg | 2.7 |
| Vitamin C | mg | 18 |
| Sodium | mg | 28 |
| Potassium | mg | 110 |
| Chloride | mg | 65 |
| Calcium | mg | 79 |
| Phosphorus | mg | 48 |
| Magnesium | mg | 8 |
| Iodine | µg | 17 |
| Iron | mg | 1 |
| Copper | µg | 65 |
| Zinc | mg | 0.8 |
| Manganese | µg | 18 |
| Selenium | µg | 2.7 |
| Choline | mg | 24 |
| Inositol | mg | 8.5 |
| Carnitine | mg | 2 |
| Taurine | mg | 6 |
| Total Nucleotides | mg | 3.1 |

Example 2

Another exemplary formulation in accordance with the present disclosure is as follows:

| Nutrient | Unit | Per 100 Kcal |
|---|---|---|
| Protein | g | 3.3 |
| Fat | g | 4.1 |
| Buttermilk | g | 3.7 |
| Linoleic Acid | mg | 640 |
| Alpha-Linolenic Acid | mg | 56 |
| Docosahexaenoic Acid | mg | 17.3 |
| Arachidonic Acid | mg | 35 |
| Carbohydrates | g | 12.8 |
| GOS | g | 0.35 |
| Polydextrose | g | 0.35 |
| Vitamin A | µg | 90 |
| Vitamin D | µg | 1.4 |
| Vitamin E | mg | 1.14 |
| Vitamin K | µg | 8 |
| Thiamin | µg | 80 |
| Riboflavin | µg | 200 |
| Vitamin B6 | µg | 70 |
| Vitamin B12 | µg | 0.5 |
| Niacin | µg | 700 |

-continued

| Nutrient | Unit | Per 100 Kcal |
|---|---|---|
| Folic Acid | μg | 16 |
| Pantothenic Acid | μg | 650 |
| Biotin | μg | 3 |
| Vitamin C | mg | 20 |
| Sodium | mg | 46 |
| Potassium | mg | 150 |
| Chloride | mg | 94 |
| Calcium | mg | 110 |
| Phosphorus | mg | 65 |
| Magnesium | mg | 9.5 |
| Iodine | μg | 22 |
| Iron | mg | 1.25 |
| Copper | μg | 68 |
| Zinc | mg | 0.76 |
| Manganese | μg | 17.8 |
| Selenium | μg | 2.5 |
| Choline | mg | 24 |
| Inositol | mg | 7 |
| Taurine | mg | 4.3 |
| Total Nucleotides | mg | 4 |
| Lactoferrin | g | 0.09 |

Example 3

Yet another exemplary formulation in accordance with the present disclosure is as follows:

Stage 3

| Nutrient | Unit | Per 100 Kcal |
|---|---|---|
| Protein | g | 3.4 |
| Fat | g | 3.7 |
| Buttermilk | g | 10 |
| Linoleic Acid | mg | 390 |
| Alpha-Linolenic Acid | mg | 38 |
| Docosahexaenoic Acid | mg | 13.9 |
| Carbohydrates | g | 13.5 |
| Dietary Fiber (Prebiotics) | g | 0.7 |
| GOS | g | 0.35 |
| Polydextrose | g | 0.35 |
| Beta-Glucan | mg | 4.9 |
| Vitamin A | μg | 97 |
| Vitamin D | μg | 1.5 |
| Vitamin E | mg | 1.11 |
| Vitamin K | μg | 7.8 |
| Thiamin | μg | 133 |
| Riboflavin | μg | 122 |
| Vitamin B6 | μg | 200 |
| Vitamin B12 | μg | 0.78 |
| Niacin | μg | 1220 |
| Folic Acid | μg | 33 |
| Pantothenic Acid | μg | 560 |
| Biotin | μg | 2.4 |
| Vitamin C | mg | 17.8 |
| Calcium | mg | 139 |
| Phosphorus | mg | 94 |
| Magnesium | mg | 13.9 |
| Sodium | mg | 51 |
| Potassium | mg | 165 |
| Chloride | mg | 111 |
| Iodine | μg | 21 |
| Iron | mg | 1.33 |
| Zinc | mg | 0.84 |
| Manganese | μg | 62 |
| Copper | μg | 83 |
| Taurine | mg | 4.4 |
| Choline | mg | 22 |
| Lactoferrin | g | 0.07 |

The nutritional composition of the present disclosure, when administered to a pediatric subject, can provide broad benefits in terms of intestinal health, immunity, healthy growth and brain development, optimally providing a synergistic combination to improve cognition and cognitive development in an infant or child.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicant reserves the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. Therefore, the spirit and scope of the appended claims should not be limited to the description of the versions contained therein.

What is claimed is:

1. A method for supporting functional neuronal maturation in a pediatric subject, the method comprising administering to the subject a nutritional composition comprising:
   up to 7 g/100 Kcal of a fat or lipid;
   up to 5 g/100 Kcal of a protein source;
   0.25 g/100 Kcal to 16 g/100 Kcal of buttermilk, wherein the buttermilk comprises 6 mg/100 Kcal to 300 mg/100 Kcal of phospholipids, 1 mg/100 Kcal to 60 mg/100 Kcal of sphingomyelin, and 0.25 mg/100 Kcal to 7.5 mg/100 Kcal of gangliosides;
   5 mg/100 Kcal to 90 mg/100 Kcal of a source of long chain polyunsaturated fatty acid, wherein the source of long chain polyunsaturated fatty acid comprises docosahexaenoic acid;
   0.015 g/100 Kcal to 1.5 g/100 Kcal of a prebiotic; and
   5 mg/100 Kcal to 300 mg/100 Kcal of lactoferrin.

2. The method of claim 1, wherein the buttermilk is present at a level of 0.6 g/100 Kcal to 15 g/100 Kcal.

3. The method of claim 1, wherein the lactoferrin is lactoferrin from a non-human source.

4. The method of claim 3, wherein the lactoferrin has at least 48% homology with human lactoferrin.

5. The method of claim 1, wherein the source of long chain polyunsaturated fatty acids further comprises arachidonic acid.

6. The method of claim 5, wherein the source of long chain polyunsaturated fatty acids is present from about 5 mg/100 Kcal to about 75 mg/100 Kcal.

7. The method of claim 6, wherein the source of long chain polyunsaturated fatty acids includes docosahexaenoic acid and arachidonic acid, at a ratio of arachidonic acid to docosahexaenoic acid of about 1:3 to about 9:1.

8. The method of claim 1, wherein the prebiotic composition comprises polydextrose and galactooligosaccharides wherein polydextrose and galactooligosaccharides comprise at least about 20% of the prebiotic composition.

9. The method of claim 8, wherein each of polydextrose is present at a level of about 0.015 g/100 Kcal to about 1.5 g/100 Kcal and galactooligosaccharides are present at a level of about 0.015 g/100 Kcal to about 1.5 g/100 Kcal.

10. The method of claim 1, wherein the nutritional composition further comprises sialic acid, short chain fatty acids, Vitamin B12, or combinations thereof.

11. The method of claim 10, wherein the short chain fatty acids are selected from the group consisting of butyric acid, caproic acid, and combinations thereof.

12. The method of claim 1, wherein the nutritional composition is an infant formula or a growing up milk.

\* \* \* \* \*